US007674476B1

(12) United States Patent
Schwertfeger et al.

(10) Patent No.: US 7,674,476 B1
(45) Date of Patent: Mar. 9, 2010

(54) USE OF AEROGELS IN AGRICULTURE

(75) Inventors: Fritz Schwertfeger, Frankfurt (DE); Andreas Zimmermann, Griesheim (DE); Gerhard Frisch, Wehrheim (DE)

(73) Assignee: Cabot Corporation, Boston, MA (US)

( * ) Notice: Subject to any disclaimer, the term of this patent is extended or adjusted under 35 U.S.C. 154(b) by 0 days.

(21) Appl. No.: 08/894,359

(22) PCT Filed: Feb. 22, 1996

(86) PCT No.: PCT/EP96/00725

§ 371 (c)(1),
(2), (4) Date: Oct. 20, 1997

(87) PCT Pub. No.: WO96/25850

PCT Pub. Date: Aug. 29, 1996

(30) Foreign Application Priority Data

Feb. 22, 1995 (DE) ................ 195 06 141

(51) Int. Cl.
*A01N 25/08* (2006.01)
(52) U.S. Cl. .............. 424/421; 424/405; 424/406; 424/409; 424/438; 424/442; 424/76.8; 424/76.9; 424/84; 43/124; 47/57.6; 504/100; 504/101; 514/918
(58) Field of Classification Search ........... 424/421, 424/724; 504/101; 71/62
See application file for complete search history.

(56) References Cited

U.S. PATENT DOCUMENTS

| 3,159,536 A | * | 12/1964 | Marotta | .............. 424/600 |
| 3,235,451 A | | 2/1966 | Franz | |
| 4,530,922 A | * | 7/1985 | Moberg | .............. 514/63 |
| 4,667,417 A | | 5/1987 | Graser | |
| 4,668,666 A | * | 5/1987 | Allan et al. | .............. 514/63 |
| 4,729,986 A | * | 3/1988 | Olson | .............. 574/63 |
| 4,927,635 A | * | 5/1990 | Loschiavo | .............. 424/409 |
| 2003/0207950 A1 | * | 11/2003 | Schwertfeger et al. | .... 516/100 |

FOREIGN PATENT DOCUMENTS

| DE | 26 52 163 | | 1/1978 |
| EP | 0 171 722 | | 8/1985 |
| EP | 171722 | | 2/1986 |
| GB | 1572718 | | 7/1980 |
| WO | WO 94/25149 | * | 11/1994 |

OTHER PUBLICATIONS

Pesticides, vol. 69, 1968, p. 8913.
Nonmammalian Biochem. vol. 92, 1980, p. 337.
Database WPI, AN 94-089171, Feb. 15, 1994.
Chemical Abstracts, vol. 69, No. 23, Dec. 2, 1968 Columbus Ohio, U.S.; abstract No. 95399, W. Ebeling, D.A. Reierson & R.E. Wagner: "Influence of repellency on the efficacy of blatticides.IV.Comparison of four cockroach species." Seite 8913; XP002007253 & J. Econ. Entomol.,B d.61, Nr.5,1968, Seiten 1213-1219.
JP63-054485 to Toray Silicone Co. Ltd.—Abstract Only (from Patent Abstracts of Japan).
International Search Report for International Patent Publication PCT/EP96/00725, mailed Aug. 6, 1996.
Chemical Abstracts, vol. 69, No. 23, Dec. 2, 1968 Columbus Ohio, U.S.; abstract No. 95399, W. Ebeling, D.A. Reierson & R.E. Wagner: "Influence of repellency on the efficacy of blatticides.IV.Comparison of four cockroach species." Seite 8913; XP002007253 & J. Econ. Entomol.,B d.61, Nr.5, 1968, Seiten 1213-1219.
JP63-054485 to Toray Silicone Co. Ltd.—Abstract Only (from Patent Abstracts of Japan), pre-1995.
International Search Report for International Patent Publication PCT/EP96/00725, mailed Aug. 6, 1996.

* cited by examiner

*Primary Examiner*—Neil Levy

(57) ABSTRACT

The present invention relates to the use of aerogels as carrier materials for active substances in agriculture and/or veterinary medicine.

22 Claims, No Drawings

USE OF AEROGELS IN AGRICULTURE

The invention relates to the use of aerogels, for example, in agriculture and veterinary medicine as carrier materials for active substances.

Aerogels, in particular those with porosities of greater than 60% and densities of less than 0.6 g/cm$^3$, have a very low thermal conductivity and are therefore used as thermal insulation material, as described, for example, in EP-A-0 171 722.

Aerogels in the wider sense, i.e. in the sense of "gel with air as dispersion medium", are prepared by drying a suitable gel. The term "aerogels" in this sense is taken to mean aerogels in the narrower sense, xerogels and cryogels, a dried gel being described as an aerogel in the narrower sense if the gel liquid is removed to a very large extent at temperatures above the critical temperature and starting from pressures above the critical pressure. If the gel liquid, in contrast, is removed subcritically, for example with formation of a liquid-vapor boundary phase, then the resultant gel is described as a xerogel.

When the term aerogels is used in the present application, it refers to aerogels in the wider sense, i.e. in the sense of "gel with air as dispersion medium".

The aerogels may, furthermore, be divided fundamentally into inorganic and organic aerogels.

Inorganic aerogels have been known from as early as 1931 (S. S. Kistler, Nature 1931, 127, 741). Since then, aerogels have been prepared from a wide variety of starting materials. Thus, for example, SiO$_2$ aerogels, Al$_2$O$_3$ aerogels, TiO$_2$ aerogels, ZrO$_2$ aerogels, SnO$_2$ aerogels, Li$_2$O aerogels, CeO$_2$ aerogels, V$_2$O$_5$ aerogels and mixtures thereof have been prepared (H. D. Gesser, P. C. Goswami, Chem. Rev. 1989, 89, 756 ff).

Organic aerogels made from a wide variety of starting materials, for example from melamine formaldehyde, have also been known for some years (R. W. Pekala, J. Mater, Sci. 1989, 24, 3221).

Inorganic aerogels can be prepared in a wide variety of ways.

For example, SiO$_2$ aerogels can be prepared by acid hydrolysis and condensation of tetraethyl orthosilicate in ethanol. This gives a gel which can be dried by supercritical drying, retaining its structure. Preparation methods based on this drying technique are known, for example, from EP-A-0 396 076 and WO 92/03378.

An alternative is provided by a process for subcritical drying of SiO$_2$ gels when these are reacted with a chlorine-containing silylating agent, before drying. The SiO$_2$ gel here can, for example, be obtained by acid hydrolysis with water of tetraalkoxysilanes in a suitable organic solvent. After exchanging the solvent for a suitable organic solvent, the resultant gel is reacted with a silylating agent in a further step. The SiO$_2$ gel thus obtained can then be dried from an organic solvent in air. In this way, aerogels with densities of less than 0.4 g/cm$^3$ and porosities of greater than 60% can be attained. The preparation process based on this drying technique is described in detail in WO 94/25149.

The abovementioned gels may moreover be mixed before drying in the aqueous alcoholic solution with tetraalkoxysilanes and aged in order to increase the strength of the gel structure, as described, for example, in WO 92/20623.

The SiO$_2$ gel can also be prepared using water glass. The preparation process based on this technique is known from DE-A-43 42 548.

In the German Patent Application No. 19502453.2, furthermore, the use of chlorine-free silylating agents is described.

Depending on the specific process used, the aerogels obtained by supercritical drying are hydrophilic or are hydrophobic for a short time. However, in the long term they are hydrophilic.

This hydrophilic character can be obviated by a hydrophobization step during the supercritical drying. A process of this type is known from EP-A-0 396 076.

Subcritically dried aerogels are permanently hydrophobic, as a result of their preparation process (silylation before drying).

It was an object of the present invention to find new applications for aerogels.

Surprisingly, it has been found that aerogels are suitable, for example, as carrier materials for active substances in agriculture and veterinary medicine.

These active materials can be insecticides, fungicides, herbicides, acaricides, piscicides, rodenticides, molluscicides, nematicides, bactericides and/or parasiticides. The aerogels can likewise serve as carrier materials for viruses, bacteria and/or bacilli, such as *Bacillus thuringensis*, for the biological control of undesirable organisms.

The active materials can be applied onto or absorbed by the aerogels in dissolved form and/or suspended in a liquid carrier medium, individually or in combinations, with the result that a quasi-liquid phase is retained in the aerogel voids described. Liquid active materials can also be absorbed without additional carrier media. For this, these liquid agents can also be provided with emulsifiers of ionic or non-ionic type. It is likewise possible to add wetting and dispersing agents to the aerogels, preferably after the active formulations have been absorbed. The size of the aerogel particles is preferably greater than 0.1 µm, particularly preferably greater than 1 µm, and in particular greater than 5 µm. The loaded aerogels may, for example, be applied onto plants, animals, fields or areas of land or water, mixed and/or diluted with at least one further carrier medium, such as talc, chalk, kaolin and/or preferably with water and/or oils.

Inorganic aerogels are preferably used. The term inorganic aerogel is taken for the purposes of the present application to mean an aerogel whose preparation has been based on inorganic materials.

The term "aerogels based on inorganic materials" is taken also to mean in particular those aerogels which are modified, for example, by silylation.

Preference is given to aerogels comprising predominantly SiO$_2$, Al$_2$O$_3$, TiO$_2$, ZrO$_2$ or mixtures thereof. Depending on their use, these can have hydrophilic and/or hydrophobic surface groups (e.g. OH, OR, R). Aerogels having hydrophilic and/or hydrophobic surface groups can be prepared by any of the processes known to a person skilled in the art. Hydrophilic or hydrophobic SiO$_2$-containing aerogels, in particular SiO$_2$ aerogels, are particularly preferred.

Surprisingly, it was also found that selection of a suitable hydrophilic or hydrophobic aerogel can accelerate or delay the liberation of corresponding materials with which the aerogel has been loaded. Aerogels can also be used as dispersants for dispersions of solid, liquid or gaseous materials in solid or liquid media. It is also possible without difficulty to incorporate hydrophilic or hydrophobic aerogels which are loaded with hydrophilic and/or hydrophobic materials into hydrophilic and/or hydrophobic, liquid, semisolid or solid media, in particular in order to introduce hydrophobic (i.e. lipophilic) materials into liquid and/or semisolid hydrophilic dispersion media, using hydrophilic aerogels, or to introduce hydrophilic materials into liquid, hydrophobic dispersion media, with the help of hydrophobic aerogels. Hydrophobic aerogels, for example, float in hydrophilic aqueous media. Even liquid hydrophilic or hydrophobic materials can moreover be converted into solid, free-flowing powders or granules.

The invention is explained below by illustrative examples, but without being restricted by these.

The preparation of, respectively, a hydrophobic and a hydrophilic aerogel is firstly described. In each of the following Examples 1 to 39 (Tables 1 to 5), both of these aerogels were employed.

In the tables, the individual constituents are in % by weight, based on the total formulation.

PREPARATIVE EXAMPLES

Example 1

Preparation of a Permanently Hydrophobic Aerogel 1 l of a sodium water glass solution (with a content of 7% by weight of $SiO_2$ and a $Na_2O:SiO_2$ ratio of 1:3.3) was stirred together with 0.5 l of an acid ion-exchange resin (styrene-divinylbenzene copolymer having sulfonic acid groups, commercially available under the name ®Duolite C20), until the pH of the aqueous solution was 2.3. The ion-exchange resin was then filtered off and the aqueous solution adjusted to pH 5.0 using 1 molar NaOH solution. The resultant gel was then aged for three hours at 85° C. and then the water was exchanged for acetone using 3 l of acetone. The acetone-containing gel was then silylated with trimethylchlorosilane (5% by weight of trimethyl-chlorosilane per gram of moist gel). The gel was dried in air (3 hours at 40° C., 2 hours at 50° C. and 12 hours at 150° C.).

The resultant transparent aerogel had a density of 0.15 $g/cm^3$ and a BET specific surface of 480 $m^2/g$ and was permanently hydrophobic.

Example 2

Preparation of a Hydrophilic Aerogel

The permanently hydrobic aerogel prepared in Example 1 was pyrolyzed at 600° C. for 1 hour in a gentle air flow, using a tubular furnace. The resultant transparent aerogel had a density of 0.18 $g/cm^3$, a BET specific surface area of 450 $m^2/g$, and was hydrophilic.

TABLE 1

| | Example | | | | | | | |
|---|---|---|---|---|---|---|---|---|
| | 1 | 2 | 3 | 4 | 5 | 6 | 7 | 8 |
| Hostathion | 20 | | | | | | | |
| Hostaquick | | 15 | | | | | | |
| Malathion | | | 18 | | | | | |
| Parathion | | | | 12 | | | | |
| Deltamethrin | | | | | 3 | | | |
| Cypermethrin | | | | | | 4 | | |
| Anilophos | | | | | | | 10 | |
| Fenthion | | | | | | | | 5 |
| Aerogel | 36.5 | 46 | 49 | 54 | 53 | 50 | 40 | 51 |
| Xylene | 30 | 25 | | | | 10 | | |
| Genapol X060 | | | 2 | 1 | 1 | | | |
| Solvesso 150 | | | 20 | | 20 | 20 | 30 | 30 |
| Emulsogen EL 400 | 6 | 5.5 | 4 | 4.5 | 3 | 2 | 6 | 5 |
| Ca dodecylbenzenesulfonate | 3 | 3.0 | 2 | 2 | 1 | 1 | 3 | 2 |
| Vanisperse CB | 4 | 4.5 | 4 | 3 | 6 | 8 | 4 | 3 |
| Hostapon T | 0.5 | 1.0 | 1.0 | 0.5 | 1 | 1 | 1 | 1 |
| Soprophor FL | | | | 3 | 2 | 4 | 1 | 2 |
| Solvesso 200 | | | | 20 | 10 | | 5 | |
| Morwet D 425 | | | | | | | | 1 |

TABLE 2

| | Example | | | | | | | |
|---|---|---|---|---|---|---|---|---|
| | 9 | 10 | 11 | 12 | 13 | 14 | 15 | 16 |
| Endosulfan | 15 | | | | | | | |
| Silafluofen | | 10 | | | | | | |
| Diclofop-methyl | | | 20 | | | | | |
| Phenoxaprop-P-ethyl | | | | 18 | | | | |
| Aerogel | 39 | 62 | 41 | 38 | 38 | 35 | 50 | 39 |
| Xylene | | | 25 | | | | | |
| Genapol X060 | | 3 | 1 | 2 | | 1 | 2 | 3 |
| Solvesso 150 | 35 | 15 | | 28 | 32 | 35 | 20 | 30 |
| Emulsogen EL 400 | 4 | | 4 | 2 | 4 | 4 | 4 | 4 |
| Ca dodecylbenzenesulfonate | 2 | | 2 | 1 | 2 | 2 | 2 | 2 |
| Vanisperse CB | | 1 | 4 | | 6 | 10 | 12 | 4 |
| Hostapon T | 1 | 1 | 1 | 1 | 1 | 1 | 2 | 1 |
| Soprophor FL | | 4 | 2 | 5 | 1 | | | 1 |
| Solvesso 200 | | | | | | | | 10 |
| Morwet D 425 | 4 | 4 | | 5 | | | | |
| Prochloraz | | | | | | 16 | | |
| Fluoxypyr | | | | | | | 12 | |
| Oxyfluorfen | | | | | | | | 8 |
| BAS 480 F | | | | | | | | 6 |

TABLE 3

| | Example | | | | | | |
|---|---|---|---|---|---|---|---|
| | 17 | 18 | 19 | 20 | 21 | 22 | 23 |
| Aerogel | 46.4 | 43.2 | 49 | 39 | 54 | 52 | 41 |
| Xylene | 25 | | | | | | |
| Genapol X060 | | 4 | 3 | | 4 | 4 | |
| Solvesso 150 | | 30 | 27.3 | 20.5 | | | |
| Emulsogen EL 400 | 6 | | | 6 | | | 4 |
| Ca dodecylbenzene-sulfonate | 3 | | | 3 | | | 2 |
| Vanisperse CB | 5 | | | 6 | | | |
| Hostapon T | 0.6 | 0.8 | 0.7 | 0.5 | 0.9 | 0.8 | 0.8 |
| Soprophor FL | 4 | 5 | 5 | | 3 | 3 | 3 |
| Solvesso 200 | | | | | 25.1 | 27.2 | 34.2 |
| Morwet D 425 | | 6 | 6 | | 5 | 5 | 5 |
| Pyrazophos | 10 | | | | | | |
| Ioxynil octanoate | | 11 | | | | | |
| Bromoxynil octanoate | | | 9 | | | | |
| CMPP butyl ester | | | | 25 | | | |
| Diflubenzuron | | | | | 8 | | |
| Propiconazol | | | | | | 8 | |
| Cyproconazol | | | | | | | 10 |

TABLE 4

| | Example | | | | | | | | |
|---|---|---|---|---|---|---|---|---|---|
| | 24 | 25 | 26 | 27 | 28 | 29 | 30 | 31 | 32 |
| Aerogel | 38 | 52 | 56 | 47 | 58 | 58 | 59 | 48 | 44 |
| Xylene | | | 5 | | | | | | |
| Genapol X060 | | | 2 | 1 | 4 | | 2 | 1 | |
| Solvesso 150 | | | 24 | 25 | 28 | 25 | | | 25 |
| Emulsogen EL 400 | 4 | 6 | | 8 | | 2 | | 5 | 6 |
| Ca dodecylbenzenesulfonate | 2 | 3 | | 4 | | 1 | | 2 | 3 |
| Vanisperse CB | | 5 | | 6 | | 5 | | | 6 |
| Hostapon T | 0.7 | 0.4 | 1 | 1 | 1 | 1 | 1 | 1 | 1 |
| Soprophor FL | 3 | | 2 | | 4 | 2 | 5 | | |
| Solvesso | 32.3 | 33.6 | | | | | 30 | 30 | |
| Morwet D 425 | 5 | | 4 | 6 | | 5 | | 5 | |
| Fenpropimorph | 15 | | | | | | | | |
| Vinclozolin | | 10 | | | | | | | |
| lambda-Cyhalothrin | | | 6 | | | | | | |
| Fluazifop-p-butyl | | | | 8 | | | | | |

TABLE 4-continued

| | \multicolumn{9}{c}{Example} |
| --- | --- | --- | --- | --- | --- | --- | --- | --- |
| | 24 | 25 | 26 | 27 | 28 | 29 | 30 | 31 | 32 |
| Cycloxydim | | | | | 9 | | | | |
| Fluoroglycophen | | | | | | 6 | | | |
| Triadimenol | | | | | | | 8 | | |
| Tridemorph | | | | | | | | 8 | |
| Metolachlor | | | | | | | | | 15 |

TABLE 5

| | \multicolumn{7}{c}{Example} |
| --- | --- | --- | --- | --- | --- | --- | --- |
| | 33 | 34 | 35 | 36 | 37 | 38 | 39 |
| Aerogel | 52 | 55 | 42 | 42 | 52 | 48 | 38 |
| Genapol X060 | 1 | 2 | | 1 | 2 | 1 | 2 |
| Solvesso 150 | | 25 | 25 | 10 | 8 | 5 | 20 |
| Isophorone | | | 10 | 24 | 25 | 25 | 20 |
| Emulsogen EL 400 | 4 | 4 | 6 | 6 | | 6 | 6 |
| Ca dodecylbenzenesulfonate | 2 | 2 | 3 | 3 | | 3 | 3 |
| Vanisperse CB | 10 | | | | | 6 | |
| Hostapon T | 1 | 1 | 1 | 1 | 1 | 1 | 1 |
| Soprophor FL | | 5 | 1 | 1 | 2 | | 5 |
| Solvesso | 25 | | | | | | |
| Morwet D 425 | | | | 4 | 4 | 5 | |
| Prosulfocarb | 5 | | | | | | |
| Cyfluthrin | | 6 | | | | | |
| Imazalil | | | 8 | | | | |
| Ethofumesate | | | | | 8 | | |
| PMP | | | | | | 5 | |
| DMP | | | | | | | 5 |
| Metamitron | | | | | | | 5 |

The invention claimed is:

1. A formulation containing at least one aerogel modified by reaction with a chlorine-containing silylating agent and further comprising at least one substance active in a field of agriculture applied onto or absorbed by the aerogel, wherein the aerogel is a carrier for said active substance and the active substance is present in the carrier in liquid, dissolved or suspended form, wherein the formulation contains at least one emulsifier.

2. The aerogel as claimed in claim 1, wherein the active substance is a fungicide.

3. The aerogel as claimed in claim 1, wherein the active substance is a herbicide.

4. The aerogel as claimed in claim 1, wherein the active substance is an acaricide.

5. The aerogel as claimed in claim 1, wherein the active is a rodenticide.

6. The aerogel as claimed in claim 1, wherein the active substance is a molluscicide.

7. The aerogel as claimed in claim 1, wherein the active substance is a nematicide.

8. The aerogel as claimed in claim 1, wherein the active substance is a bactericide.

9. The aerogel as claimed in claim 1, wherein the active substance is a parasiticide.

10. The formulation of claim 1, wherein the active substance is in dissolved form.

11. The formulation of claim 1, wherein the active substance is suspended in a liquid carrier medium.

12. A formulation containing at least one aerogel modified by reaction with a chlorine-containing silylating agent and further comprising at least one substance active in a field of agriculture applied onto or absorbed by the aerogel, wherein the aerogel is a carrier for said active substance and the active substance is present in the carrier in liquid, dissolved or suspended form, wherein the formulation contains at least one wetting and dispersing agent.

13. The formulation as claimed in claim 12 wherein the active substance is a fungicide.

14. The formulation as claimed in claim 12 wherein the active substance is a herbicide.

15. The formulation as claimed in claim 12 wherein the active substance is an acaricide.

16. The formulation as claimed in claim 12 wherein the active substance is a rodenticide.

17. The formulation as claimed in claim 12 wherein the active substance is a molluscicide.

18. The formulation as claimed in claim 12 wherein the active substance is a nematicide.

19. The formulation as claimed in claim 12 wherein the active substance is a bactericide.

20. The formulation as claimed in claim 12 wherein the active substance is a parasiticide.

21. The formulation of claim 12, wherein the active substance is in dissolved form.

22. The formulation of claim 12, wherein the active substance is suspended in a liquid carrier medium.

* * * * *